(12) United States Patent
Park

(10) Patent No.: US 10,251,791 B2
(45) Date of Patent: Apr. 9, 2019

(54) PHIMOSIECTOMY SHIELD

(71) Applicant: COZYELL CO., LTD., Incheon (KR)

(72) Inventor: Eun-Ha Park, Siheung-si (KR)

(73) Assignee: COZYELL CO., LTD., Incheon (KR)

( * ) Notice: Subject to any disclaimer, the term of this patent is extended or adjusted under 35 U.S.C. 154(b) by 331 days.

(21) Appl. No.: 15/124,347

(22) PCT Filed: Mar. 17, 2015

(86) PCT No.: PCT/KR2015/002552
§ 371 (c)(1),
(2) Date: Sep. 7, 2016

(87) PCT Pub. No.: WO2015/142022
PCT Pub. Date: Sep. 24, 2015

(65) Prior Publication Data
US 2017/0014274 A1    Jan. 19, 2017

(30) Foreign Application Priority Data

Mar. 18, 2014  (KR) ........................ 10-2014-0031403

(51) Int. Cl.
A61F 13/00 (2006.01)
A61F 13/471 (2006.01)
A61F 13/02 (2006.01)

(52) U.S. Cl.
CPC .. *A61F 13/00038* (2013.01); *A61F 13/00046* (2013.01); *A61F 13/025* (2013.01); *A61F 13/471* (2013.01); *A61F 2013/00093* (2013.01); *A61F 2013/00272* (2013.01)

(58) Field of Classification Search
USPC ........................................... 602/70; D24/189
See application file for complete search history.

(56) References Cited

U.S. PATENT DOCUMENTS

| | | | | |
|---|---|---|---|---|
| 1,615,945 A | * | 2/1927 | James | A61F 6/02 602/42 |
| 5,183,460 A | * | 2/1993 | Scherz | A61F 13/023 128/844 |
| 5,935,091 A | * | 8/1999 | Friedman | A61F 13/148 128/844 |
| 6,580,011 B1 | * | 6/2003 | Jennings-Spring | A61F 13/00021 602/41 |

(Continued)

FOREIGN PATENT DOCUMENTS

KR   20-1992-0008787 Y1   12/1992
KR   20-1993-0017777 U    8/1993

(Continued)

*Primary Examiner* — Kim M Lewis
(74) *Attorney, Agent, or Firm* — Rabin & Berdo, P.C.

(57) ABSTRACT

A phimosiectomy shield can be firmly fixed to a human body to be able to stably protect an operated part after phimosiectomy, reduces pain in the operated part by stably preventing pressure and friction on the operated part, and helps an operated part to quickly recover by stably preventing bacterial infection due to contact. The phimosiectomy shield includes a protective part surrounding a penis to protect an operated part due to phimosiectomy and an attachment part extending from the protective part to be attached to a human body, in which a hole for inserting a penis is formed at the center of a lower portion of the attachment part.

6 Claims, 10 Drawing Sheets

(56) References Cited

U.S. PATENT DOCUMENTS

| | | | |
|---|---|---|---|
| 7,905,852 B2* | 3/2011 | Jennings-Spring | ............................ A61F 13/00063 602/48 |
| 8,211,044 B2* | 7/2012 | Liebowitz | ................. A61F 5/10 602/22 |
| 2007/0197983 A1 | 8/2007 | Giles Finn | |
| 2013/0144201 A1* | 6/2013 | Becker | .............. A61F 13/00085 602/43 |

FOREIGN PATENT DOCUMENTS

KR  10-2007-0064318 A  6/2007
KR  10-2013-0005730 A  1/2013

\* cited by examiner

PHIMOSIECTOMY SHIELD

TECHNICAL FIELD

The present invention relates to a phimosiectomy shield. More particularly, it relates to a phimosiectomy shield that can be firmly fixed to a human body after phimosiectomy, to stably protect an operated part of the body, reduce pain in the operated part by stably preventing pressure and friction on the operated part, and help an operated part to quickly recover by stably preventing bacterial infection due to contact.

BACKGROUND ART

In medical parlance, phimosiectomy is also called circumcision and is a surgical operation for exposing the glans by removing an appropriate length of the foreskin (skin covering the glans). Circumcision of newborn babies is common in western countries, but phimosiectomy is usually performed in the age of puberty in Korea.

A patient feels intense pain in the operated part after phimosiectomy. In particular, since patients wear clothes, the pain becomes more severe when the operated part is pressed by underwear or pants or when the operated part rubs on clothes.

Accordingly, most patients use a protector such as a paper cup to reduce pain so that an operated part is kept inside the paper cup without being pressed by clothes such as underwear or pants, thereby reducing pain due to pressure and friction.

However, though using a paper cup can prevent an operated part from being pressed by clothes, when a patient moves the operated part is still touched, for example, it hits against the inner side of the paper cup because the inside of the paper cup is large, so pain is still caused.

Accordingly, a "Protector for using an operation for phimosis" has been proposed in Korean Utility Model Application Publication No. 20-1992-0008787, which is characterized in that, as shown in FIGS. 1 and 2, a protector body 1 having a plurality of vents has an inclined portion 2 at the rear side and a front open side 3, and is assembled in a cylindrical shape with a joint A by a tape 5, in which an adhesive band 6 can be attached to the top of the rear portion to be attached directly to a skin.

However, though the protector disclosed in Korean Utility Model Application Publication No. 20-1992-0008787 has the advantage of being able to reduce pain due to pressure or friction by clothes by covering an operated part with the protector in close contact with the outer side of the operated part, only the upper portion of the protect is brought in contact with a human body, so the protector may be easily separated. Further, despite the protector being made of thick paper or vinyl, it is still difficult to completely block the pressure to the operated part in the protector from clothes and thus pain is still caused.

Further, since vents having a predetermined size are formed through the protector, bacteria may enter the protector through the vents, so an operated part may not quickly heal.

DISCLOSURE

Technical Problem

The present invention has been proposed to solve the problems in the related art. An object of the present invention is to provide a phimosiectomy shield that includes a protective part for protecting an operated part and an attachment part being attached to a human body to fix the protective part and that allows an attachment part to be firmly attached to a human body by inserting the penis in a hole formed at the center of a lower portion of the attachment part and then attaching an adhesive sheet on the attachment part to the human body, and that can prevent the shield from being unexpectedly separated by covering an operated part from under with the protective part extending from the lower end of the attachment part.

Another object of the present invention is to provide a phimosiectomy shield that includes shape maintainers made of metal such as aluminum and which are arranged with regular intervals on the bottom of the protective part for protecting an operated part so that the protective part can keep its shape even if pressure is applied by clothes, whereby it can prevent pressure from being directly applied to the operated part and prevent pain due to pressure applied to the operated part.

Another object of the present invention is to provide a phimosiectomy shield that allows an operated part to quickly heal by preventing bacterial infection due to contact, by using non-woven fabric having high air permeability for the protective part for protecting an operated part and by disposing a filter layer made of a material such as nanofiber web or NT209T (fabricated by mixing nylon and polyester fiber) on the top or the bottom of the protective part.

Technical Solution

In order to achieve the above object, according to one aspect of the present invention, there is provided a phimosiectomy shield including: a protective part surrounding the penis to protect an operated part; and an attachment part extending from the protective part to be attached to the human body.

A hole for inserting the penis may be formed at a lower portion of the attachment part.

The protective part may extend from a lower end of the attachment part to be bendable.

Shape maintainers may be disposed on a bottom of the protective part.

The shape maintainers may be made of metal in thin bar shapes and arranged with regular intervals.

A filter layer may be disposed on a top or a bottom of the protective part.

The attachment part may be formed to correspond to a size of a pubic hair area around the penis.

The attachment part may be attached to the human body by an adhesive sheet on a front side thereof.

The protective part may be coupled to a lower portion of the attachment part by sewing or by an adhesive.

Advantageous Effects

According to the phimosiectomy shield that includes a protective part for protecting an operated part and an attachment part being attached to the human body to fix the protective part, it is possible to allow an attachment part to be firmly attached to the human body by inserting the penis in a hole formed at the center of a lower portion of the attachment part and then attaching an adhesive sheet on the attachment part to the human body. Further it is also possible prevent the shield from being unexpectedly separated by covering an operated part from under with the protective part extending from the lower end of the attachment part.

According to the phimosiectomy shield, it includes shape maintainers made of metal such as aluminum and which are arranged with regular intervals on the bottom of the protective part for protecting an operated part so that the protective part can keep its shape even if pressure is applied by clothes, whereby it can prevent pressure from being directly applied to the operated part and prevent pain due to pressure applied to the operated part.

Further, according to the phimosiectomy shield, it is possible to allow an operated part to quickly heal by preventing bacterial infection due to contact, by using non-woven fabric having high air permeability for the protective part for protecting an operated part and by disposing a filter layer made of a material such as nanofiber web or NT209T (fabricated by mixing nylon and polyester fiber) on the top or the bottom of the protective part.

MODE FOR INVENTION

Figure 1:
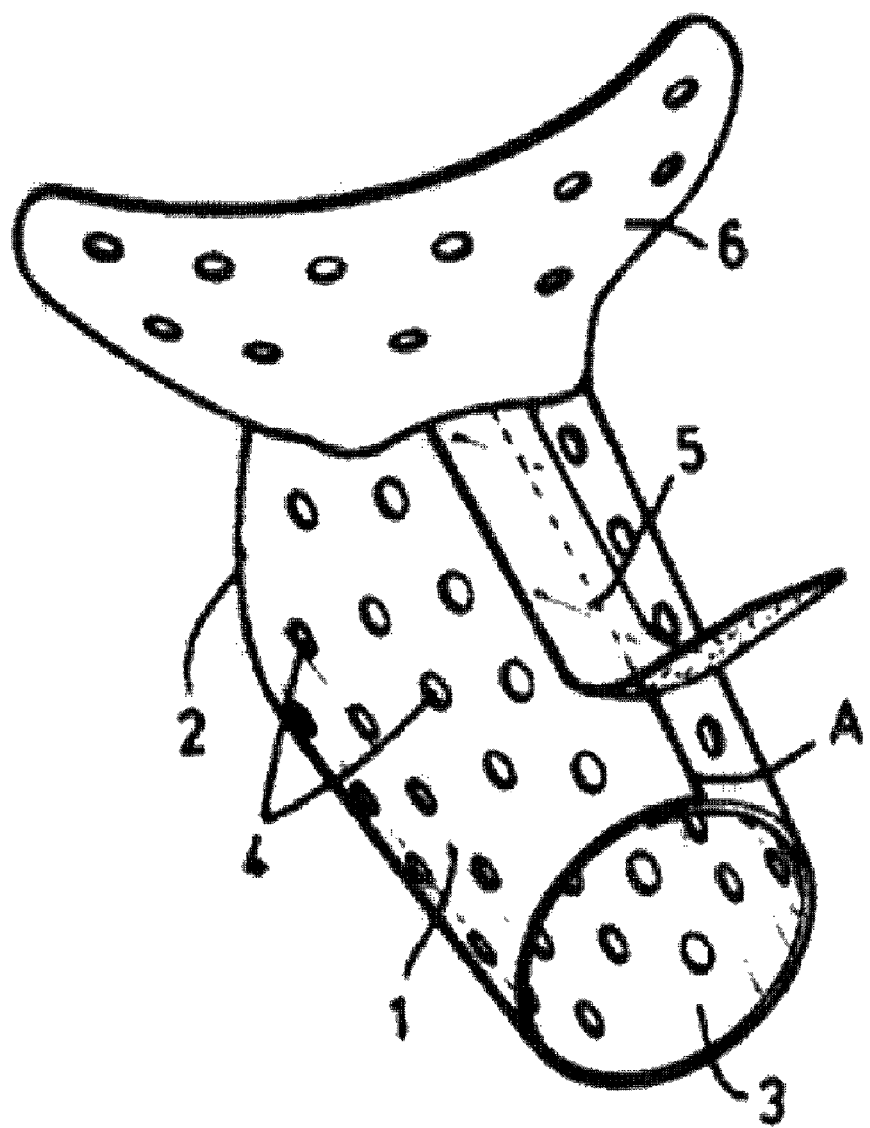
FIG. 1 is a perspective view of a protector for use in an operation for phimosis of the related art.

Hereinafter, exemplary embodiments of the present invention will be described in detail with reference to the accompanying drawings. The same components are given the same reference numerals in the drawings and a repeated description is not provided for the same components. Further, it should be understood that the present invention may be achieved in various ways and is not limited to the embodiments described herein.

Figure 3:
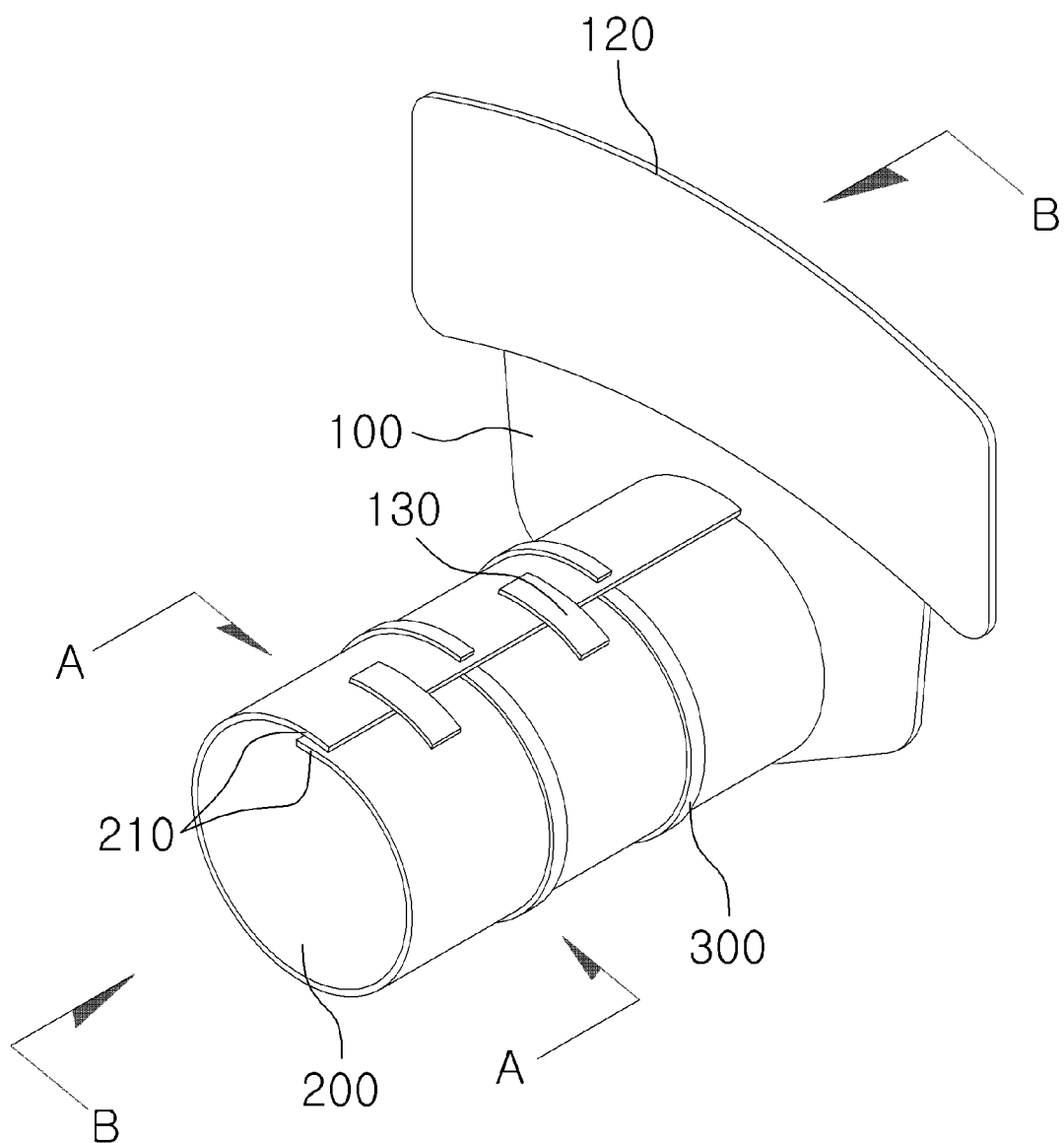
FIG. 3 is a perspective view of a phimosiectomy shield according to the present invention.
Figure 4:
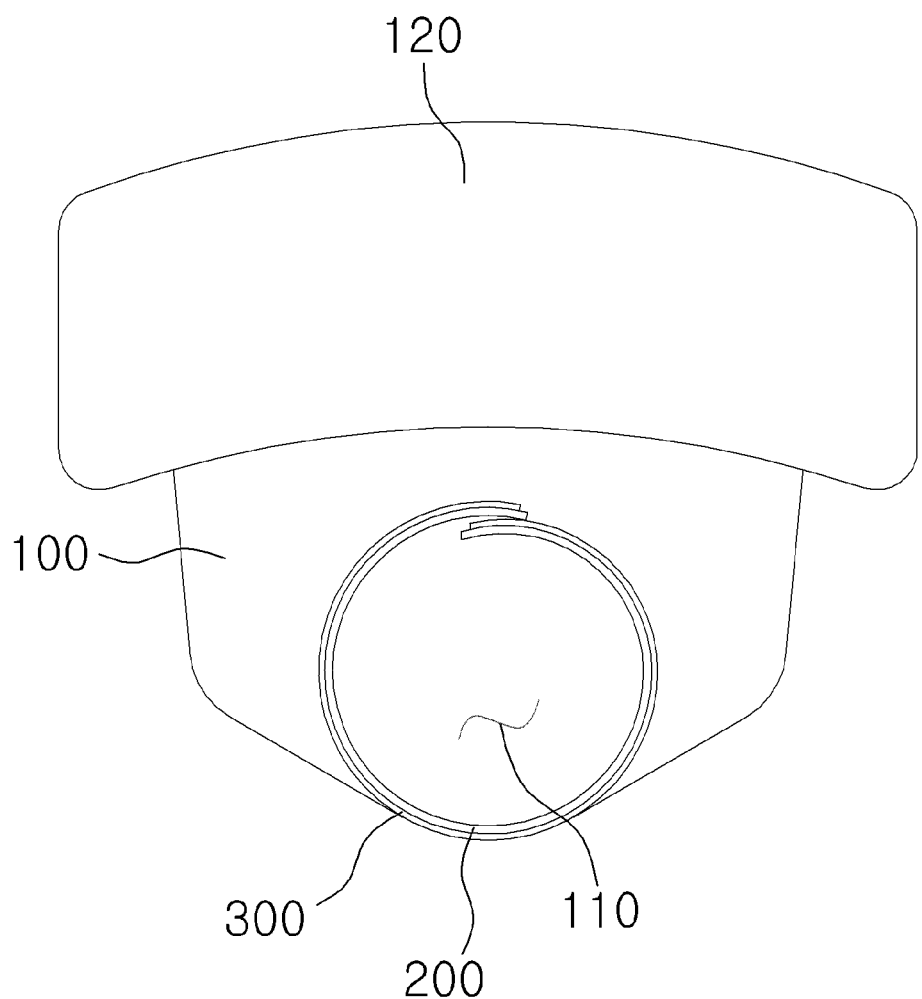
FIG. 4 is a cross-sectional view taken along line A-A of FIG. 3.
Figure 5:
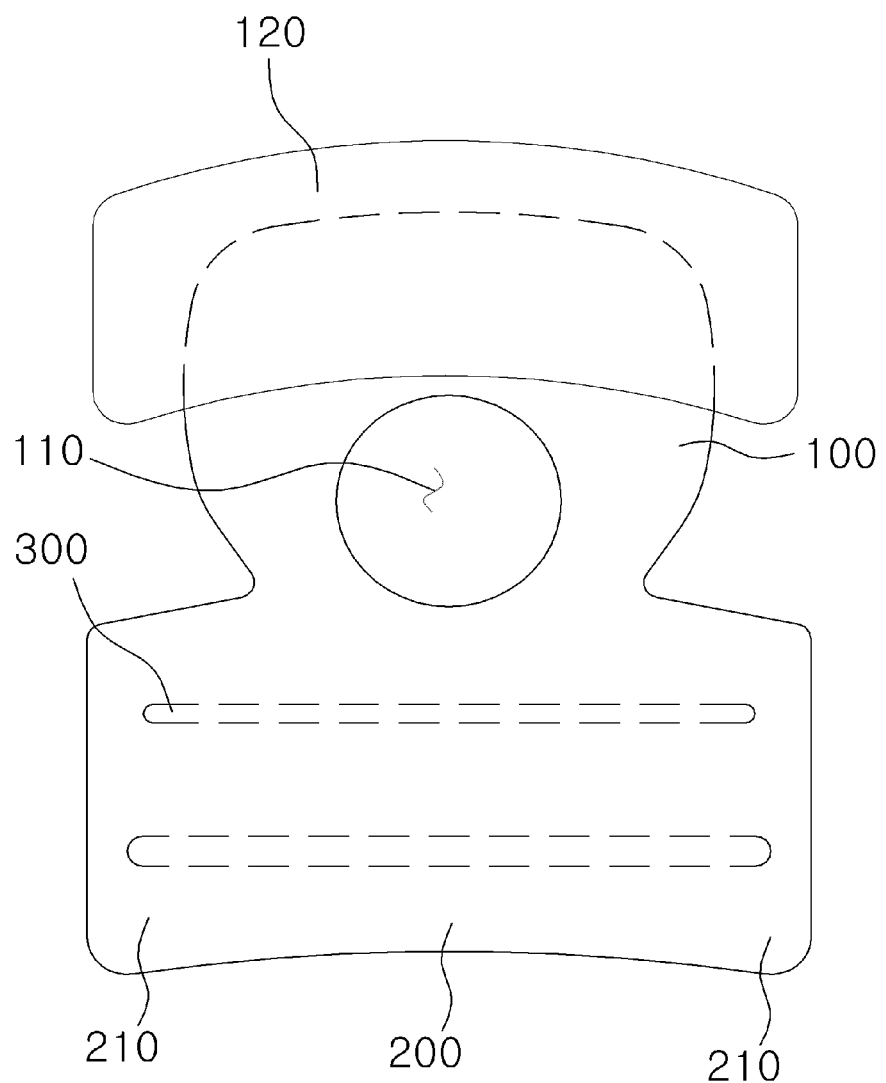
FIG. 5 is a development view of the phimosiectomy shield according to the present invention.
Figure 6:
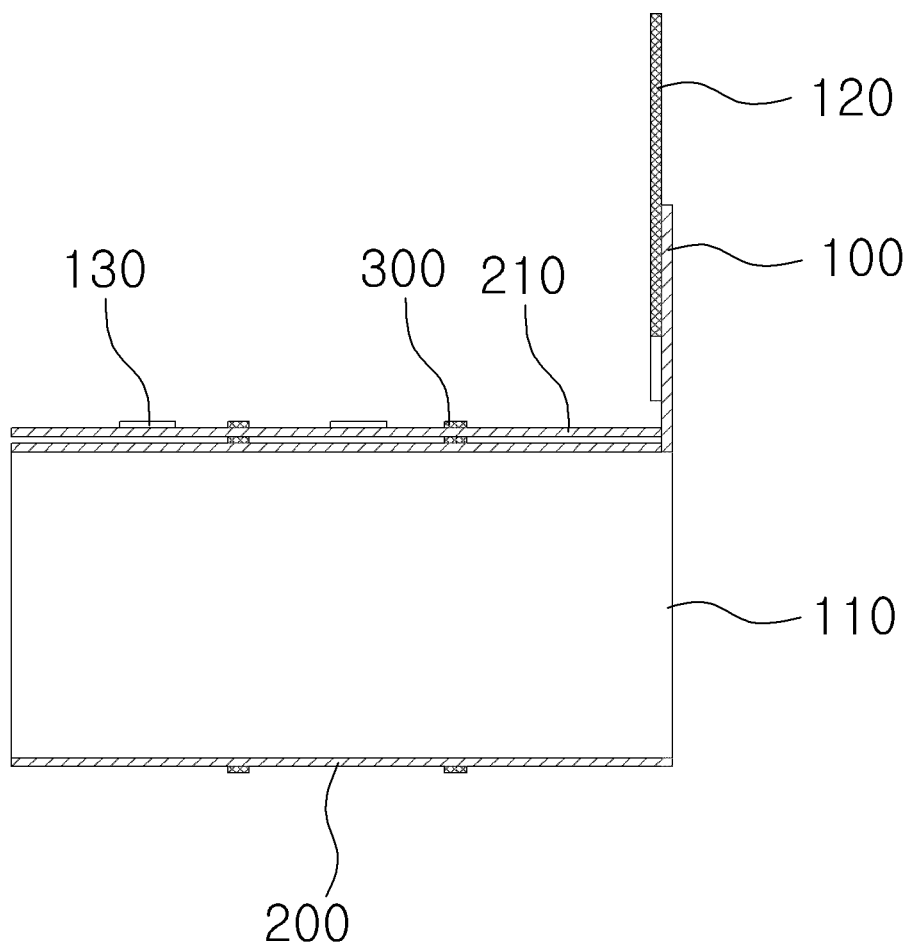
FIG. 6 is a cross-sectional view taken along line B-B of FIG. 3.
Figure 7:
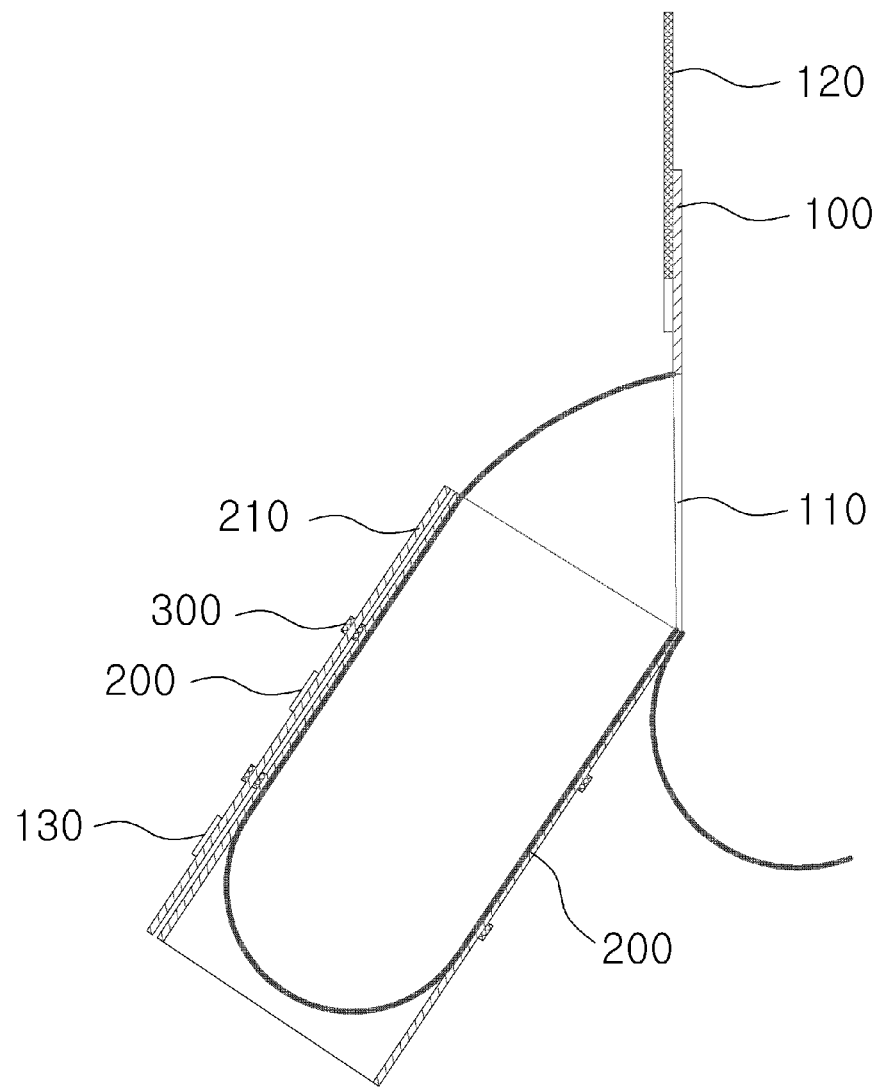
FIG. 7 is a partial cross-sectional view of a phimosiectomy shield according to another embodiment of the present invention.
Figure 8:
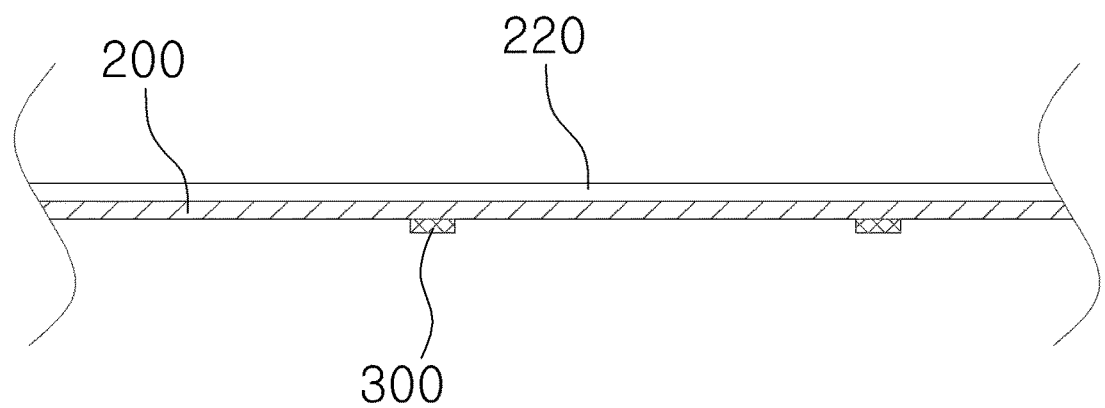
FIG. 8 is a cross-sectional view when a phimosiectomy shield according to the present invention is used.

FIG. 3 is a perspective view of a phimosiectomy shield according to the present invention, FIG. 4 is a cross-sectional view taken along line A-A of FIG. 3, FIG. 5 is a development view of the phimosiectomy shield according to the present invention, FIG. 6 is a cross-sectional view taken along line B-B of FIG. 3, FIG. 7 is a partial cross-sectional view of a phimosiectomy shield according to another embodiment of the present invention, and FIG. 8 is a cross-sectional view when a phimosiectomy shield according to the present invention is used.

The present invention relates to a phimosiectomy shield for use after phimosiectomy for reducing pain in an operated part by protecting the operated part. As shown in FIGS. 3 to 6, the phimosiectomy shield includes a protective part 200 for protecting an operated part of the penis of a patient and an attachment part 100 that is disposed on the protective part 200 to be attached to the human body.

The protective part 200 has wings 210 to cover the penis, but patients have different sizes of penises, so operated parts of patients are protected by appropriately covering the operated part with the wins 210.

Further, the attachment part 100 has a hole 110 at the center of a lower portion to insert the penis of a patient in the through hole 110. The size of the attachment part 100 is determined to correspond to the size of the pubic hair region around the penis of the patient.

Accordingly, when a penis is inserted into the hole 110 of the attachment part 100, the attachment part 100 covers all of the pubic hair, so it is possible to firmly attach the attachment part 100 to the human body using an adhesive sheet 120.

Figure 2:
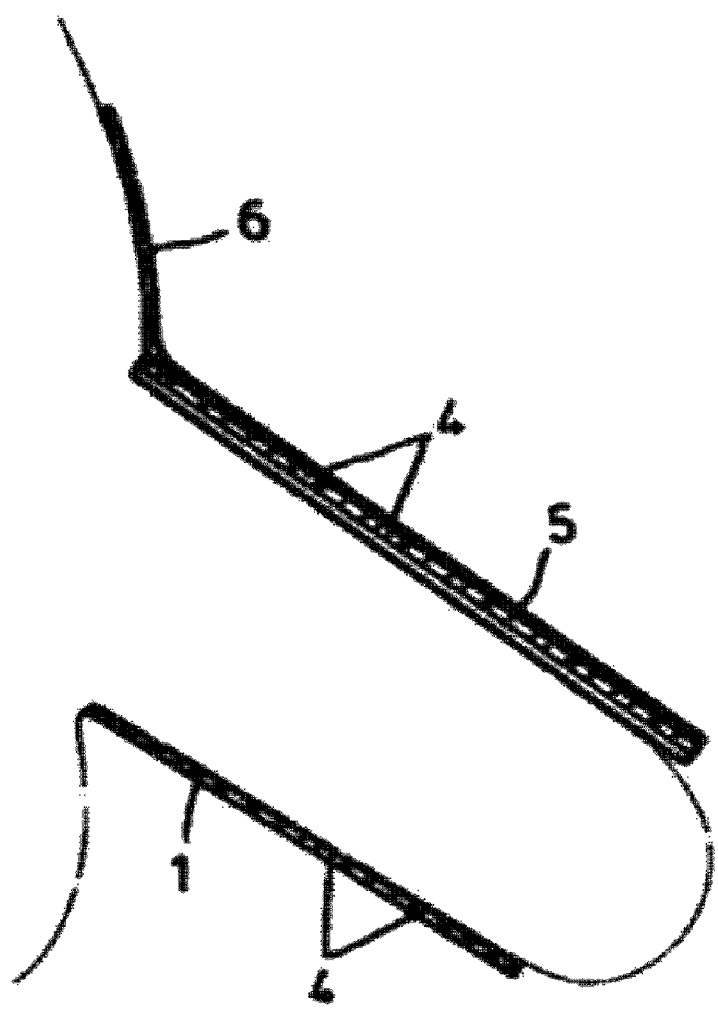
FIG. 2 is a cross-sectional view when a user wearing the protector for use in an operation for phimosis of the related art.

That is, as shown in FIGS. 1 and 2, when a protector is attached to a human body in the related art, an adhesive band 6 is disposed at the rear end of a body 1 and is directly attached to the pubic hair around the penis, so the adhesive force is insufficient and it easily come off. However, the attachment part 100 of the present invention is attached to the human body after attaching the adhesive sheet 100 to the front of the attachment part 100. The adhesive sheet 120 is disposed over the hole 110 at the center of the attachment part 100 with the upper end and the sides protruding out of the attachment part 100, so the portions of the adhesive sheet 120 protruding from the upper portion and sides of the attachment part 100 are attached to the body of the patient. Accordingly, it is not attached to the pubic hair, so it can be firmly attached.

The adhesive sheet 120 may be separately provided, but it may be attached to the upper portion of the attachment part 100 in advance, in which a separator (not shown) is disposed on the back of the adhesive sheet 120 to prevent the adhesive sheet 120 is unexpectedly attached.

The adhesive sheet 120 is disposed on the front of the attachment part 100 and the separator for protecting the adhesive sheet 120 is disposed on the back of the attachment part 100.

Further, the protective part 200 extends from the lower portion of the attachment part 100 and can bend on the lower end of the attachment part 100, so it can move with the penis of a patient, whereby it is possible to stably protect an operated part.

Shape maintainers 300 are disposed on the bottom of the protective part 200 and are made of metal such as aluminum in thin bar shapes.

The shape maintainers 300 are disposed on the back of the protective part 200, perpendicular to the longitudinal direction of a penis and are arranged with regular intervals in the longitudinal direction of the protective part 200.

Further, when a patient attaches the attachment part 100 to his body and bends the wings 210 of the protective part 200 around the penis, the shape maintainers 300 bend to fit to the shape of the penis.

Accordingly, the shape maintainers 300 maintain their shapes corresponding to the shape of the patient's penis, so even if an operated part is pressed for example by clothes that the patient wears, the pressure is reduced by the force for maintaining the shape of the shape maintainers 300. Therefore, pain due to force pressing the operated part of the patient is reduced.

Further, since the protective part 200 bends to surround the patient's penis, the ends of the wings 210 at both sides of the protective part 200 overlap each other and the overlapping portions are fixed to the wings 210 by specific assistant adhesive sheets 130, so the operated part of the patient is more stably protected.

Further, the protective part 200 is made of a material having high air permeability, that is, non-woven fabric, so air can easily flow through the protective part even though an operated part of a patient is covered, whereby it is possible to stably prevent the operated part from irritation.

Nano-silver fibers may be disposed in the protective part 200, and in this case, bacterial infection of an operated part is prevented, so the operate part can quickly heal.

Meanwhile, as another embodiment of the present invention, as shown in FIG. 7, a protective part 100 for protecting an operated part of a patient is made of non-woven fabric having high air permeability and a separate filter layer 220 is disposed on the protective part 100.

The filter layer 220 may be disposed on the bottom of the protective part 100.

The filter layer 220 is made of a material, for example a nanofiber web or N209T (fabricated by fixing nylon and polyester fiber), that can block fine particles, so the non-woven fiber of the protective part 100 primarily filters particles having a predetermined or more size and the filter layer 220 further filters them. Accordingly, it is possible to stably prevent fine particles from coming in contact with the operated part of a patient.

Accordingly, air can easily come in contact with the operated part of a patient, while particles such as dirt are prevented from coming in contact with the operated part. Therefore, the operated part of a patient is prevented from being inflamed and irritation by dirt is prevented so that the operated part can quickly heal.

Figure 9:
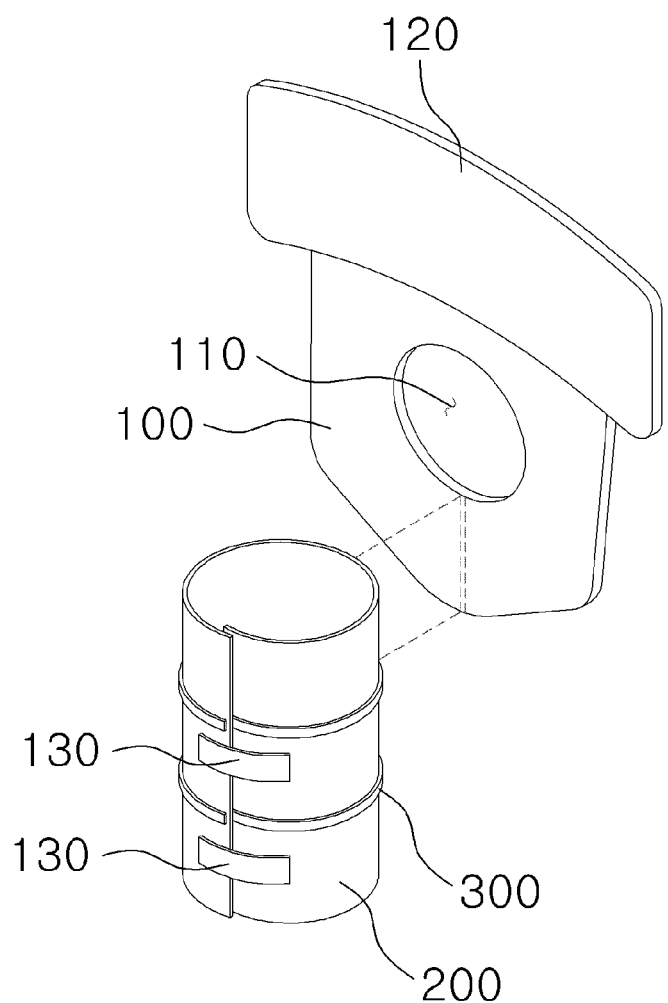
FIG. 9 is an exploded perspective view of a phimosiectomy shield according to another embodiment of the present invention.
Figure 10:
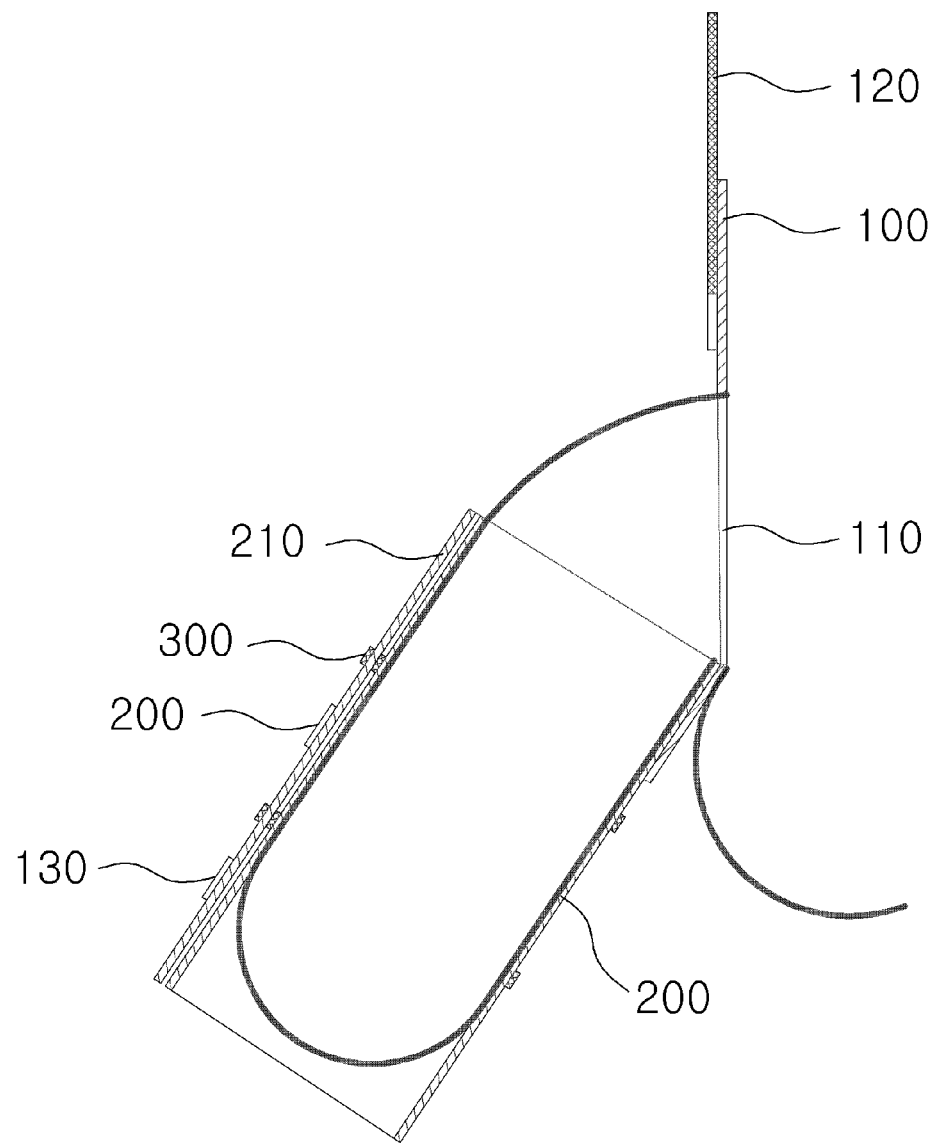
FIG. 10 is a cross-sectional view when the phimosiectomy shield shown in FIG. 9 is used.

Further, another embodiment of the present invention, as shown in FIGS. 9 and 10, includes a protective part 200 for protecting an operated part of the penis of a patient, for example due to phimosiectomy, and an attachment part 100 disposed on the protective part 200 to be attached to the human body.

The protective part 200 and the attachment part 100 are separately manufactured and then the protective part 200 is coupled to the attachment part. The upper rear side of the protective part 200 is bonded by applying an adhesive to the front side of a lower portion of the attachment part 100, that is, the front side under a hole 110 formed at the center of the attachment part 100 or the protective part 200 and the attachment part 100 are sewn to be firmly coupled to each other.

When sewing or an adhesive is used, the protective part 200 is rolled, the protective part 200 is put on the attachment part 100 such that a portion of the protective part and the lower portion of the attachment part are brought in line contact with each other, and then sewing or bonding is performed, whereby the protective part 200 can more easily bend.

The other configuration is the same as those described above, so it is not described in detail here.

Although embodiments of the present invention were described above, the scope of the present invention is not limited thereto, the present invention may be modified in various ways by those skilled in the art without departing from the spirit of the present invention, and modifications substantially equivalent to the embodiments of the present invention are also included in the scope of the present invention.

INDUSTRIAL APPLICABILITY

The present invention relates to a phimosiectomy shield and, more particularly, to a phimosiectomy shield that can be firmly fixed to a human body to be able to stably protect an operated part after phimosiectomy, reduces a pain in the operated part by stably preventing pressure and friction on the operated part, and helps an operated part to quickly recover by stably preventing bacterial infection due to contact.

What is claimed is:

1. A phimosiectomy shield comprising:
a protective part including wings bending and configured to surround a penis to protect an operated part thereof, each end of the wings at each side of the protective part overlapping each other, and the overlapped protective part being fixed to the wings by assistant adhesive sheets:
a plurality of shape maintainers disposed on a back of the protective part, perpendicular to a longitudinal direction of the penis and arranged with regular intervals in a longitudinal direction of the protective part; and
an attachment part disposed on the protective part configured to be attached to a human body to fix the protective part, the protective part being coupled to a lower portion of the attachment part by sewing or by an adhesive for allowing the attachment part to be firmly attached to a human body by inserting the penis in a hole formed at the center of the lower portion of the attachment part, wherein
the attachment part is formed to correspond to a size of a pubic hair area around the penis, wherein
the attachment part is configured to be attached to a human body for covering the size of a pubic hair area; and
an adhesive sheet being attached on a front side of the attachment part to prevent the attachment part from being unexpectedly separated from under with the protective part which extends from the lower portion of the attachment part, and wherein
the adhesive sheet is attached to an upper portion of the attachment part and is configured to be attached directly to a skin not covering the pubic hair.

2. The phimosiectomy shield of claim 1, wherein a hole for inserting a penis is formed at a lower portion of the attachment part.

3. The phimosiectomy shield of claim 2, wherein the protective part extends from a lower end of the attachment part to be bendable.

4. The phimosiectomy shield of claim 1, wherein shape maintainers are disposed on a bottom of the protective part.

5. The phimosiectomy shield of claim 4, wherein the shape maintainers are made of metal in thin bar shapes and are arranged with regular intervals.

6. The phimosiectomy shield of claim 1, wherein a filter layer is disposed on a top or a bottom of the protective part.

* * * * *